(12) United States Patent
Stokes et al.

(10) Patent No.: US 11,529,171 B2
(45) Date of Patent: Dec. 20, 2022

(54) IMAGE-GUIDED TRANSSEPTAL PUNCTURE DEVICE

(71) Applicant: CardiacAssist, Inc., Pittsburgh, PA (US)

(72) Inventors: Jerry Stokes, Sarver, PA (US); John C Marous, III, Pittsburgh, PA (US)

(73) Assignee: CardiacAssist, Inc., Pittsburgh, PA (US)

( * ) Notice: Subject to any disclaimer, the term of this patent is extended or adjusted under 35 U.S.C. 154(b) by 287 days.

(21) Appl. No.: 15/125,898

(22) PCT Filed: Mar. 16, 2015

(86) PCT No.: PCT/US2015/020733
§ 371 (c)(1),
(2) Date: Sep. 13, 2016

(87) PCT Pub. No.: WO2015/139031
PCT Pub. Date: Sep. 17, 2015

(65) Prior Publication Data
US 2017/0014159 A1    Jan. 19, 2017

Related U.S. Application Data

(60) Provisional application No. 61/953,011, filed on Mar. 14, 2014.

(51) Int. Cl.
*A61B 17/34* (2006.01)
*A61B 8/12* (2006.01)
(Continued)

(52) U.S. Cl.
CPC ........ *A61B 17/3478* (2013.01); *A61B 1/3137* (2013.01); *A61B 5/0086* (2013.01);
(Continued)

(58) Field of Classification Search
CPC .. A61B 17/34; A61B 8/12; A61B 8/00; A61B 5/00; A61B 5/05; A61B 34/20;
(Continued)

(56) References Cited

U.S. PATENT DOCUMENTS 4,790,825 A    12/1988  Bernstein et al.
5,190,528 A    3/1993   Fonger et al.
(Continued)

OTHER PUBLICATIONS

Rosso et al. "Transseptal Puncture: A Step-by-Step Procedural Guide", Cardiac Interventions Today, May/Jun. 2019, p. 22-26 (Year: 2019).*

(Continued)

*Primary Examiner* — Keith M Raymond
*Assistant Examiner* — Amy Shafqat
(74) *Attorney, Agent, or Firm* — Seager, Tufte & Wickhem LLP

(57) ABSTRACT

Provided herein is a catheter assembly including an imaging device for identifying an anatomical structure. The catheter assembly includes a patient cannula configured to be drawn along a catheter or guide wire; a transseptal puncture catheter at least partially enclosed within the patient cannula; and an imaging catheter. The imaging catheter includes a transducer configured to emit an energy beam capable of reflecting from an anatomical structure and to detect energy reflected from the structure. The catheter assembly also includes a transmitter for conveying a signal representative of the detected energy from the transducer to a signal processor for obtaining information about the structure. An imagining system and a method for identifying a predetermined transseptal puncture location on an atrial septum are also provided herein.

12 Claims, 11 Drawing Sheets

(51) Int. Cl.

| | | |
|---|---|---|
| *A61B 5/05* | (2021.01) | |
| *A61B 8/00* | (2006.01) | |
| *A61B 5/107* | (2006.01) | |
| *A61B 34/20* | (2016.01) | |
| *A61B 1/313* | (2006.01) | |
| *A61B 5/00* | (2006.01) | |
| *A61B 17/00* | (2006.01) | |
| *A61B 5/0205* | (2006.01) | |
| *A61B 5/0215* | (2006.01) | |
| *A61B 8/08* | (2006.01) | |
| *A61B 6/12* | (2006.01) | |
| *A61B 8/04* | (2006.01) | |

(52) U.S. Cl.
CPC .............. *A61B 5/05* (2013.01); *A61B 5/1076* (2013.01); *A61B 5/742* (2013.01); *A61B 5/7405* (2013.01); *A61B 8/12* (2013.01); *A61B 8/445* (2013.01); *A61B 8/4416* (2013.01); *A61B 8/4477* (2013.01); *A61B 34/20* (2016.02); *A61B 5/0084* (2013.01); *A61B 5/0205* (2013.01); *A61B 5/0215* (2013.01); *A61B 6/12* (2013.01); *A61B 8/04* (2013.01); *A61B 8/0883* (2013.01); *A61B 2017/00247* (2013.01); *A61B 2017/3413* (2013.01)

(58) Field of Classification Search
CPC ... A61B 1/313; A61B 17/3478; A61B 1/3137; A61B 5/0086; A61B 5/7405; A61B 5/742; A61B 8/4416; A61B 2017/3413; A61B 2017/00247; A61B 5/1076; A61B 8/4477; A61B 8/445; A61B 5/0084; A61B 5/0205; A61B 5/0215; A61B 8/0883; A61B 8/04; A61B 6/12; A61B 2017/348; A61B 2017/00252; A61B 2017/3482; A61B 5/1075
See application file for complete search history.

(56) References Cited

U.S. PATENT DOCUMENTS

| | | | |
|---|---|---|---|
| 5,711,753 A | 1/1998 | Pacella et al. | |
| 6,099,514 A * | 8/2000 | Sharkey | A61M 25/0133 604/264 |
| 6,258,086 B1 * | 7/2001 | Ashley | A61B 17/1671 604/510 |
| 6,650,923 B1 * | 11/2003 | Lesh | A61B 17/3478 600/407 |
| 6,808,508 B1 | 10/2004 | Zafirelis et al. | |
| 6,863,653 B1 | 3/2005 | Fanelli et al. | |
| 7,226,417 B1 | 6/2007 | Eberle et al. | |
| 8,147,414 B2 | 4/2012 | Abraham | |
| 8,369,932 B2 * | 2/2013 | Cinbis | A61B 5/0075 600/424 |
| 8,550,973 B2 | 10/2013 | Magovern et al. | |
| 8,562,519 B2 | 10/2013 | Smith et al. | |
| 8,608,661 B1 * | 12/2013 | Mandrusov | A61B 5/6852 424/484 |
| 8,622,949 B2 | 1/2014 | Zafirelis et al. | |
| 9,173,646 B2 * | 11/2015 | Fabro | A61B 17/00234 |
| 9,622,706 B2 * | 4/2017 | Dick | A61B 5/0062 |
| 10,639,060 B2 * | 5/2020 | Vardi | A61B 17/32053 |
| 2003/0195496 A1 | 10/2003 | Maguire et al. | |
| 2004/0073110 A1 * | 4/2004 | Stewart | A61B 8/0883 600/437 |
| 2006/0009715 A1 | 1/2006 | Khairkhahan et al. | |
| 2006/0276710 A1 * | 12/2006 | Krishnan | A61B 5/042 600/424 |
| 2007/0156048 A1 | 7/2007 | Panescu et al. | |
| 2007/0197896 A1 | 8/2007 | Moll et al. | |
| 2007/0293724 A1 | 12/2007 | Saadat et al. | |
| 2008/0249397 A1 * | 10/2008 | Kapadia | A61B 17/3478 600/424 |
| 2009/0048668 A1 * | 2/2009 | Wilson | A61F 2/246 623/2.36 |
| 2011/0087175 A1 | 4/2011 | Krishnan | |
| 2011/0245582 A1 | 10/2011 | Zafirelis et al. | |
| 2013/0030521 A1 * | 1/2013 | Nitzan | A61B 17/0057 623/2.13 |
| 2013/0116522 A1 | 5/2013 | Cinbis et al. | |
| 2013/0172758 A1 | 7/2013 | de Marchena | |
| 2013/0237743 A1 | 9/2013 | Kassab et al. | |
| 2014/0031686 A1 | 1/2014 | Kim et al. | |
| 2014/0180273 A1 * | 6/2014 | Nair | A61N 7/022 606/34 |
| 2014/0221842 A1 | 8/2014 | Castelino et al. | |
| 2014/0277054 A1 * | 9/2014 | McNamara | A61B 17/3403 606/185 |
| 2016/0008636 A1 * | 1/2016 | Warnking | A61B 8/0841 600/411 |
| 2017/0199654 A1 * | 7/2017 | Wu | A61B 5/055 |
| 2019/0029705 A1 * | 1/2019 | Vardi | A61B 17/32053 |
| 2020/0170662 A1 * | 6/2020 | Vardi | A61B 17/32053 |

OTHER PUBLICATIONS

Image Sensor—CCD vs. CMOS (Wikipedia) Feb. 27, 2014 <https://web.archive.org/web/20140227144734/https://en.wikipedia.org/wiki/Image_sensor>.

\* cited by examiner

IMAGE-GUIDED TRANSSEPTAL PUNCTURE DEVICE

CROSS-REFERENCE TO RELATED APPLICATIONS

This application is the United States national phase of International Application No. PCT/US2015/020733 filed Mar. 16, 2015, and claims priority to United States Provisional Patent Application No. 61/953,011 filed Mar. 14, 2014, the disclosures of which are hereby incorporated in their entirety by reference.

BACKGROUND OF THE INVENTION

Field of the Invention

This disclosure relates to a system and method for transseptal puncture from the right atrium to the left atrium and, more specifically, to systems and methods for transseptal puncture from the right atrium to the left atrium using an invasive catheter having an imaging sensor or device.

Description of Related Art

Numerous cardiac procedures require providing catheter access to the left atrium, either for removing blood from the left atrium (e.g., venting) through a catheter or cannula or for performing various interventional procedures therein. For example, a circulatory support system for use during cardiac surgery, heart transplantation, or after failed coronary intervention requires that fluid communication between the left atrium and a blood pump is established. Such fluid communication allows for providing oxygenated blood through the circulatory system via an external pump. Similarly, circulatory support systems can increase cardiac output of oxygenated blood by using an external fluid pump to drawn oxygenated blood from the left atrium, thus bypassing or assisting the patients native pumping mechanism, the left ventricle. Additionally, numerous percutaneous cardiac procedures require access to the left atrium including, treatment or removal of the left atrial appendage, electrophysilogy (EP) ablation, heart catheterization for hemodynamic monitoring, mitral valve repair or replacement, treatment of para-valvular leaks, and similar procedures.

A preferred method for providing access to the left atrium with a catheter is referred to as transseptal puncture or left atrial cannulation; see U.S. Pat. No. 8,550,973 to Magovern and U.S. Pat. No. 8,622,949 to Zafirelis et al., each of which are incorporated herein by reference in their entireties, for a brief description of a method of transseptal puncture or left atrial cannulation. A transseptal puncture or cannulation system including a catheter and guide wire is inserted into the femoral vein and advanced through the vein toward the right atrium of the heart. Once the catheter and guide wire enter the right atrium, the distal end of the catheter is oriented toward the septum between the right and left atria. When the distal end of the catheter is positioned adjacent the septum in the right atrium, the guide wire is withdrawn from the catheter orifice and a needle assembly moves past the guide wire and through the catheter orifice to a position adjacent to the septum. The needle pierces the septum and the catheter moves over the needle assembly to further dilate the septal hole. The cannula attached to the catheter also moves through the septal hole providing additional dilation force. The guide wire, the needle assembly, and the catheter are withdrawn from the cannula. Oxygenated blood from the left atrium drains through the cannula to an extracorporeal pump and back to the body through an arterial cannula.

U.S. Pat. No. 4,790,825 to Bernstein et al. illustrates a similar method of transseptal left atrial cannulation. In Bernstein, a guide wire and catheter are inserted into the femoral vein, and the guide wire directs the catheter through the veins to the right atrium. Once the catheter is in place, the guide wire is withdrawn from the catheter and a needle is directed through the length of the catheter and into the right atrium. The needle is used to pierce the inter-atrial septum, and the catheter is advanced over the needle into the left atrium. The needle is then removed from the catheter and an obturator (with a circular barb for attaching to the catheter hub) is directed through the entire length of the catheter and into the right atrium. An external obturator extension is then screwed on to the internal obturator, and a cannula is threaded over the entire length of the catheter and obturator. Once the cannula is in place, the cannula tip extends across the atrial septum and into the left atrium. Finally, the catheter and the obturator are removed from the interior of the cannula. Beneficially, this insertion and removal procedure can be used to provide sufficient access to the left atrium without needing to perform a thoracotomy.

The thickness of the atrial septum varies over the length of the septum. The thickest portion of the septum is near the top of the atrium, and the thickness decreases toward the middle third of the septum. The thinnest portion of the atrial septum is referred to as the fossa ovalis. It is generally desirable to insert the needle assembly through the thinnest portion of the septum. Therefore, it is often necessary to determine the position of the guide wire and catheter relative to the septum prior to insertion of the needle assembly. Previously, surgeons determined the location of the fossa ovalis portion of the atrial septum based on feel or contact between the septum and needle prior to insertion. However, a need exists for imaging systems and methods for better determining position of the distal end of the catheter in the heart and vasculature of a patient.

Various visualization systems are known and may be used to assist in placement of the needle assembly. For example, fluoroscopy is often used to assist in positioning of the catheter and needle. Other imaging tools including intracardiac echocardiography and transesophageal echocardiograph (TEE) can also be used to assist in needle placement. Such imaging systems advantageously provide real time visualization of the internal anatomy of the heart. However, these systems require a separate imaging device that accesses the heart either via a separate venous access point or by placement down the esophagus.

Invasive visualization systems are used for identification and diagnosis of coronary artery disease, as well as for identification of cardiac structures to aid in placement of devices. These systems can be coupled to a catheter and provided in conjunction with ablation electrodes or other surgical tools. The difficulty of providing visualization sensors, such as ultrasonic transducers, on such small catheters has led to a number of distinct technical solutions. For example, some catheters include a single rotating transducer. These are capable of producing high quality images, but suffer from image distortion due to vibration of the tip and non-uniform rotation of the transducer, problems caused by the long, flexible rotating drive shaft. Another approach is to have a multi-element transducer capable of emitting ultrasonic pulses in a radial direction from a number of distinct transducers. This approach is described in U.S. Pat. No. 7,226,417 to Eberle et al. entitled "High resolution intravascular ultrasound transducer assembly having a flexible substrate" and assigned to Volcano Corporation, and incorporated herein in its entirety. Such catheter systems including radially projecting multi-element ultrasonic transducers, referred to as Intravascular Ultrasound (IVUS) systems, are commercially available from a number of sources' including Volcano Corporation, of San Diego, Calif.

SUMMARY OF THE INVENTION

In view of the foregoing, there is a need for a modified venous imaging catheter for use in transseptal puncturing procedures that provides improved imaging of the atrial septum and positioning of the transseptal puncture apparatus. Therefore, the present disclosure generally relates to systems and methods for performing a transseptal puncture for providing access to the left atrium of the human heart. The systems and methods use various invasive or intravascular imaging catheters to assist in identification of structures in the right atrium and for positioning of the transseptal puncture apparatus.

According to one aspect of the disclosure, a catheter assembly includes a patient cannula configured to be drawn along a catheter or guide wire; a transseptal puncture catheter at least partially enclosed within the patient cannula; and an imaging catheter. The imaging catheter includes a transducer configured to emit an energy beam capable of reflecting from an anatomical structure and to detect energy reflected from the structure. The catheter assembly also includes a transmitter for conveying a signal representative of the detected energy from the transducer to a signal processor for obtaining information about the structure.

In some embodiments, the transseptal puncture catheter includes an introducer and a transseptal needle. In addition, the imaging catheter can be enclosed within, co-formed, or integrated with the patient cannula. Alternatively, the imaging catheter can extend parallel with and be connected to an outer surface of the patient cannula.

In some embodiments, the energy beam emitted from the transducer includes ultrasonic waves, radio waves, visible light waves, infrared waves, ultraviolet waves, or any combination thereof. Alternatively, the energy beam includes an electro-magnetic signal. In that case, the reflected electromagnetic signal detected by the transducer is indicative of a thickness of the structure to be identified.

In some embodiments, the imaging catheter includes a plurality of transducers located around an outer surface of the imaging catheter and positioned to obtain a 360 degree image. Each of the plurality of transducers can be positioned to emit the energy beam in a radial direction relative to a longitudinal axis of the imaging catheter. Alternatively, each of the plurality of transducers can be positioned to emit the radiation beam in an axial direction. In other embodiments, the transducer is located on a distal face of the imaging catheter and is positioned to emit the energy beam in an axial direction.

According to another aspect of the disclosure, an imaging system includes a catheter assembly, a signal processor configured to receive a signal from a transmitter and to process the signal to obtain information about an anatomical structure; and a visual and/or audio display configured to receive the information about the anatomical structure from the signal processor to provide the information to an operator. The catheter assembly includes a patient cannula configured to be drawn along a catheter or guide wire, a transseptal puncture catheter at least partially enclosed within the patient cannula, and an imaging catheter. The imaging catheter includes a transducer configured to emit an energy beam capable of reflecting from an anatomical structure and to detect energy reflected from the anatomical structure. The catheter assembly also includes a transmitter for conveying a signal representative of the detected energy from the transducer.

In some embodiments, the information about the structure comprises a real time image of the anatomical structure. The information about the structure can also include a thickness of the anatomical structure. The system can also include a power supply, wherein power provided by the power supply is conveyed to the transducer through the transmitter.

According to another aspect of the disclosure, a method for identifying a predetermined transseptal puncture location on an atrial septum is provided. The method includes providing a catheter assembly comprising a patient cannula, a transseptal puncture catheter, and an imaging catheter. The imaging catheter includes a transducer configured to emit an energy beam capable of reflecting from an anatomical structure and to detect energy reflected from the structure. The catheter assembly also includes a transmitter for conveying a signal representative of the detected energy from the transducer to a signal processor for obtaining information about the anatomical structure. The method also includes the steps of: directing the patient cannula along a guide wire to a position in a right atrium of a patient; directing the imaging catheter to the right atrium; passing the imaging catheter along at least a portion of the atrial septum, such that the energy beam is emitted toward the atrial septum; detecting energy reflected from the atrial septum with the transducer; and identifying, based on the detected reflected energy, a predetermined location of the atrial septum for performing a transseptal puncture.

In some embodiments, directing the imaging catheter to the right atrium includes advancing the imaging catheter through the patient cannula along the same guide wire used to direct the patient cannula. The predetermined location of the atrial septum for performing the transseptal puncture can be a portion of the fossa ovalis. Further, in some embodiments, the patient cannula enters the right atrium through the superior vena cava.

In some embodiments, passing the imaging catheter along a portion of the atrial septum includes bending a distal end of the imaging catheter toward the superior vena cava at about a 45 degree angle relative to the longitudinal axis of the imaging catheter, and retracting the imaging catheter into the superior vena cava to draw a distal end of the imaging catheter along a portion of the atrial septum.

In some embodiments, the method also includes performing the transseptal puncture at the predetermined location with the transseptal puncture catheter.

BRIEF DESCRIPTION OF THE DRAWINGS

Some of the advantages and features of the preferred embodiments have been summarized hereinabove. These embodiments, along with other potential embodiments will become apparent to those skilled in the art when referencing the following drawings in conjunction with the detailed descriptions as they relate to the figures.

DESCRIPTION OF THE INVENTION

Figure 1:
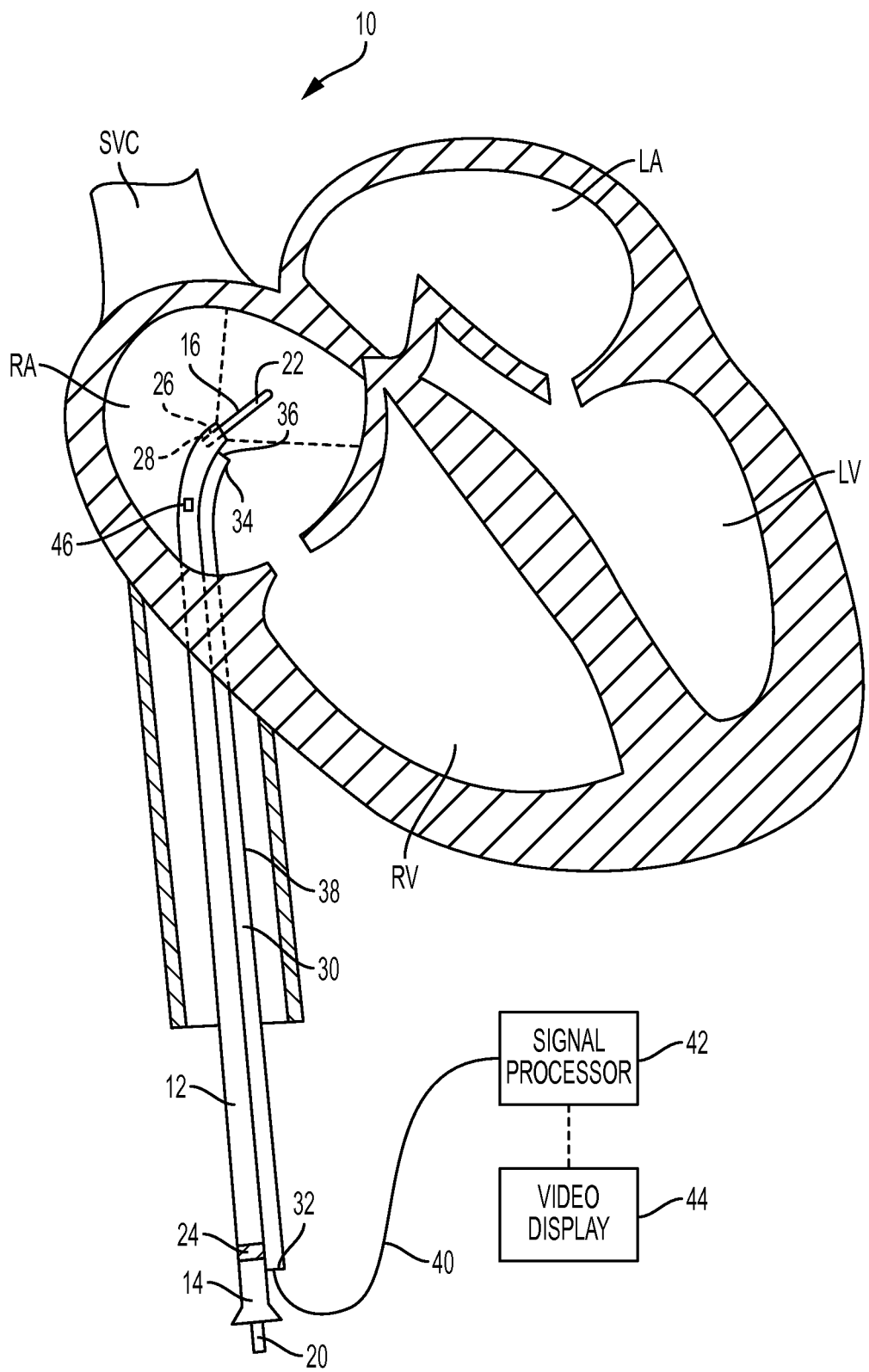
FIG. 1 is a schematic drawing of a system for performing transseptal puncture.

The illustrations generally show preferred embodiments of the systems and methods of the present invention. While the descriptions present various embodiments of the devices, it should not be interpreted in any way as limiting the invention. Furthermore, modifications, concepts, and applications of the invention's embodiments are to be interpreted by those skilled in the art as being encompassed, but not limited to, the illustrations and descriptions herein.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

Further, for purposes of the description hereinafter, the terms "end", "upper", "lower", "right", "left", "vertical", "horizontal", "top", "bottom", "lateral", "longitudinal" and derivatives thereof shall relate to the invention as it is oriented in the drawing figures. The term "proximal" refers to the direction toward the center or central region of the device. The term "distal" refers to the outward direction extending away from the central region of the device. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting. For the purpose of facilitating understanding of the invention, the accompanying drawings and description illustrate preferred embodiments thereof, from which the invention, various embodiments of its structures, construction and method of operation, and many advantages may be understood and appreciated.

Figure 1A:
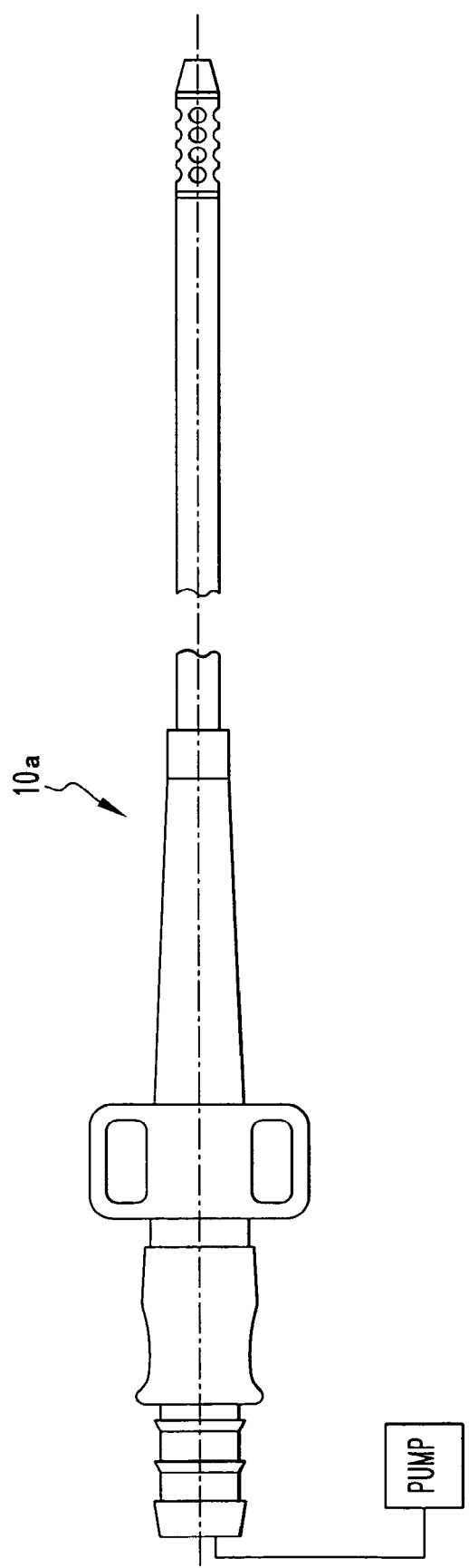
FIG. 1A is a schematic drawing of the patient cannula and transseptal puncture catheter, according to an aspect of the disclosure.
Figure 1B:
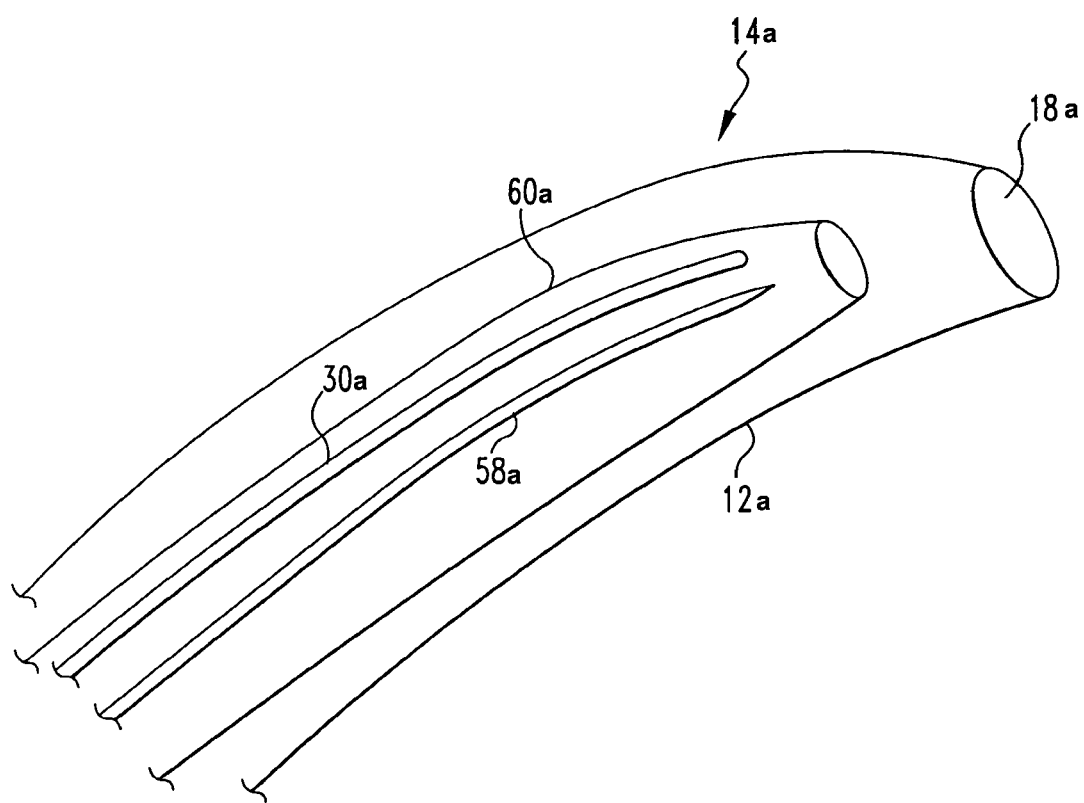
FIG. 1B is a schematic drawing of a distal end of the transseptal puncture catheter of FIG. 1A.

With reference to FIGS. 1A and 1B, a cannula 12a for performing a transseptal puncture procedure is illustrated. In the operation, a distal end 14a of the cannula 12a is inserted into a patient at a vascular access site and advanced to the right atrium of the patient's heart via the femoral vein. Generally, this occurs in the following way. A guide wire 30a is introduced into the patient and threaded to the right atrium of the patient. The guide wire 30a can be about a 0.035 inch wire formed from a super stiff material that is at least about 260 cm long. The cannula 12a and a second catheter 60a including a needle 58, such as a transseptal puncture catheter, are placed over the end of the guide wire 30a, such that the guide wire 30a extends through an orifice 18a of the cannula 12a and an opening in the second catheter 60. The cannula 12a and second catheter 60a are then inserted into the patient and moved along the guide wire 30a to the right atrium of the patient. When the distal end 14a of the cannula 12a is in the right atrium, the guide wire 30a is pulled back 46a into the cannula 12a freeing the orifice 18a so there is nothing in the orifice 18a. The needle 58a and the second catheter 60a are then advanced so the second catheter 60a extends through the orifice 18a and the needle 58a extends through the opening of the second catheter 60a. The needle 58a and second catheter 60a are then forced into the septum until they puncture the septum and move into the left atrium. The needle 58a is then retracted from the opening of the second catheter 60a, and the guide wire 30a is moved forward through the second catheter's opening into the left atrium. The second catheter 60a is maintained in position while the guide wire 30a is maintained in place in the left atrium. The cannula 12a is then advanced forward into the left atrium along the guide wire 30a and the second catheter 60a which extend through the orifice 18a. The presence of the second catheter 60a acts as a stiffener for the cannula 12a to assist in the placement of the cannula 12a in the left atrium. The second catheter 60a, needle 58a and guide wire 30a are then removed from the cannula 12a. Cannulas and transseptal puncturing catheters that can be used for performing the above-described procedures are disclosed, for example, in U.S. Pat. No. 5,190,528 to Fonger et al. and U.S. Pat. No. 8,622,949 to Zafirelis et al., each of which is incorporated herein in its entirety. Another suitable transseptal puncturing device is described in U.S. Pat. No. 8,562,519 to Smith et al., which is also incorporated herein by reference in its entirety.

Figure 2:
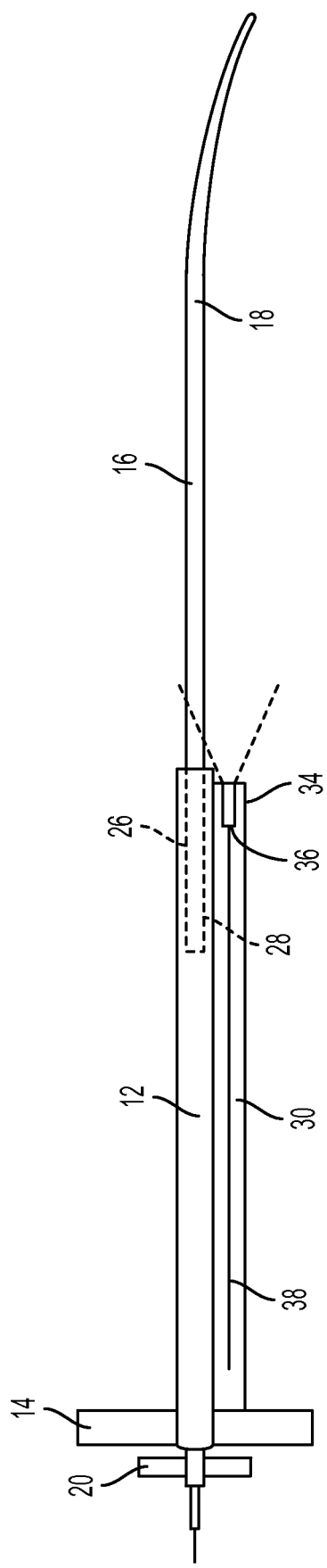
FIG. 2 is a schematic drawing of a transseptal catheter or cannula and patient cannula.

Having generally described a cannula and transseptal puncture catheter that can be used for a transseptal puncture procedure and with reference to FIGS. 1 and 2, a system 10 for performing a transseptal puncture procedure with the aid of an electronic imaging apparatus is now discussed in detail. The system 10 includes one or more catheters or lumens arranged to perform a transseptal puncture procedure. The catheters can be arranged in a concentric orientation, an eccentric orientation, or integrally formed as a unitary structure. The catheters can be integrated into a larger system including apparatus for performing a transseptal puncture, a system for cardiac assist or ventricular bypass, and/or systems for performing surgical or therapeutic treatments in the left atrium.

A first or outer most lumen, referred to hereinafter as a patient cannula 12, is a standard transseptal catheter lumen consisting of a catheter hub 14 at its most proximal end. More specifically, the patient cannula 12 is an elongated cannula or tube that is about 65 cm to 75 cm in length. The patient cannula 12 is formed from a suitable flexible material, such as polyurethane. The patient cannula 12 can be wire reinforced permitting a catheter with a thin-walled construction. The patient cannula 12 can include various radiopaque markings to assist in positioning and steering of the patient cannula 12 with the aid of fluoroscopic guidance. The patient cannula 12 can be any gauge suitable for insertion through an insertion site, such as the right femoral vein. For example, the patient cannula 12 can be a 21 Fr tube and, in some embodiments, can contain a guide wire. The guide wire is not preformed, but can be bent by the user prior to insertion. The needle retains the bent shape and imparts the same bent shape to the patient cannula 12. The needle has sufficient shape memory, yet is sufficiently flexible, to follow the shape of a vein without losing its curve once it moves into the atrium.

The second lumen, referred to as a transseptal catheter 16, includes an introducer 18 that includes a proximal hub 20 configured to accept a needle assembly including a guide wire and/or a standard transseptal needle 22. The purpose of the introducer 18 is to guide the cannula assembly over the guide wire to provide placement of a patient cannula 12. The guide wire can be a standard 0.032 or 0.035 inch wire. The needle 22 can be a single metal tube with a narrowed distal end that projects out of the catheter orifice. For example, a Brockenbrough needle or similar needle structure can be used with the transseptal catheter 16. The distal end of the introducer 18 can be maneuverable or steerable so that the angle of the distal end or tip changes to engage variations in atrial septal anatomy. The proximal end of the introducer 18 can include a hemostatsis valve 24 or cap to prevent blood loss. Generally, the transseptal catheter 16 is a narrower gauge than the patient cannula 12, such as about 14 Fr.

The transseptal catheter 16 can further include a dilator 26, which is a slightly stiffer structure, inserted into the cannula 12 and introducer 18 assembly. The dilator 26 serves to dilate the hole in the fossa ovalis and to facilitate insertion of the patient cannula 12 to the left atrium. The dilator 26 can be a Mullins dilator. The transseptal catheter 16 can also include an obturator 28 that seals or controls fluid access to the catheter to prevent blood and other fluids from collecting in the catheter.

With continued reference to FIGS. 1 and 2, the third catheter is an imaging catheter 30. The imaging catheter 30 includes an elongated tube extending from a proximal end 32, which remains outside the body throughout the procedure, to a distal end 34, which is configured to be inserted into the body at a vascular access site. The imaging catheter 30 can be any size suitable for insertion through the vascular access site though, in many embodiments, the imaging catheter 30 is narrower than either the patient cannula 12 or transseptal catheter 16. For example, the imaging catheter 30 can be between about 3 and 10 Fr. The patient cannula 12 and imaging catheter 30 can be concentric or eccentric but arranged to form a cylindrical shaft. Alternatively, the imaging catheter 30 can be integrated or co-formed with the patient cannula 12 to form a uniform body.

The imaging catheter 30 includes one or more transducers 36 for emitting energy and for detecting a reflected response to record an image. The energy signal can include or be in the form of ultrasound, radio waves, light waves, or another energy signal that reflects from a solid structure to provide information concerning the shape and appearance of the structure. However, for good image quality, the emitted energy signal should be capable of projecting through a high viscosity fluid such as blood. A user or system operator can review the obtained images to determine the location of the patient catheter 12 or to identify structures such as the atrial septum.

In another embodiment, the transducers 36 are electromagnetic transducers that emit and detect an electro-magnetic signal for measuring thickness of a structure, such as the atrial septum. In use, a transducer 36 of the imaging sensor 30 is placed on or adjacent to a structure, such as the atrial septum. An electro-magnetic wave is emitted through the septum and feedback from blood flow on the opposite side of the structure is detected and measured. When the transducer 36 is placed against the thin fossa ovalis portion of the septum, a stronger electro-magnetic feedback signal is detected. When the transducer 36 is placed on or adjacent to thicker portions of the septum, a weaker feedback signal is detected. In this manner, the electro-magnetic transducers 36 provide evidence of thickness of the atrial septum. Therefore, electro-magnetic detection allows the user to identify thin portions of the atrial septum without being required to visually identify the region from images of the septum surface.

With continued reference to FIGS. 1 and 2, a shaft of the imaging catheter 30 can include electronic circuitry 38, such as a wired or wireless data transmitter or communications interface, that controls, transmits data from, and provides power to the transducers 36. For example, the electronic circuitry 38 can be wired or wirelessly connected to an external power supply for providing power to the transducers 36. Further, the proximal end 32 of the imaging catheter 30 can include a conduit enclosing a cord 40 that connects the transducer 36 to a signal processor 42 for controlling, processing, or measuring a signal received from the transducer 36. The signal processor 42 can be connected to a visual and/or audio display 44 that is configured to project or provide information about an anatomical structure to a user or operator. For example, the visual and/or audio display 44 can show a real time image of the anatomical structure or can provide physical characteristics, such as the thickness or surface properties, of the structure. In some embodiments, the image shown on the visual display 44 can include a Doppler flow enhanced image. In addition, in the case where the electronic circuitry 38 includes a wireless transmitter, data can be sent to an external source, such as a remote signal processor 42 or another remote computer system or database for further analysis and storage. In some embodiments, the transducers 36 can receive power or recharge from energy provided to the transducer 36 through the wireless transmitter.

With continued reference to FIGS. 1 and 2, the imaging catheter 30 includes a transducer 36 positioned on the sidewall of the catheter 30 near its distal end 34. The transducer 36 is positioned to emit an expanding radiation beam, such as an ultrasound signal or pulse, beyond the distal end 34 of the catheter 30. For example, the transducer 36 can be a raised structure with an axially facing emitter than projects a signal beyond the distal end 34 of the catheter 30. The transducer 36 is configured to record reflectance of the emitted pulse or signal. Since the catheter 30 only includes one transducer 36, the user may need to rotate or otherwise maneuver the catheter 30 to obtain useful visual images of surrounding structures.

Figure 3A:
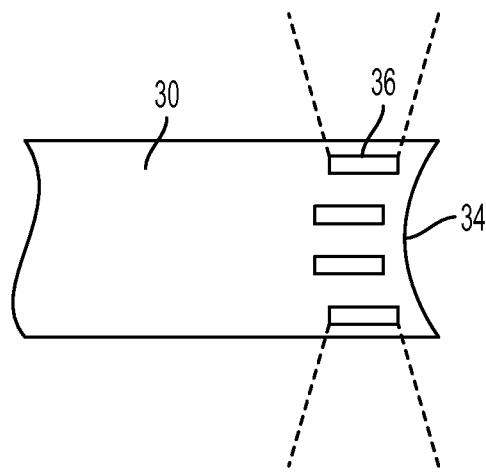
FIG. 3A is a schematic drawing of a perspective view of an embodiment of an imaging catheter.
Figure 3B:
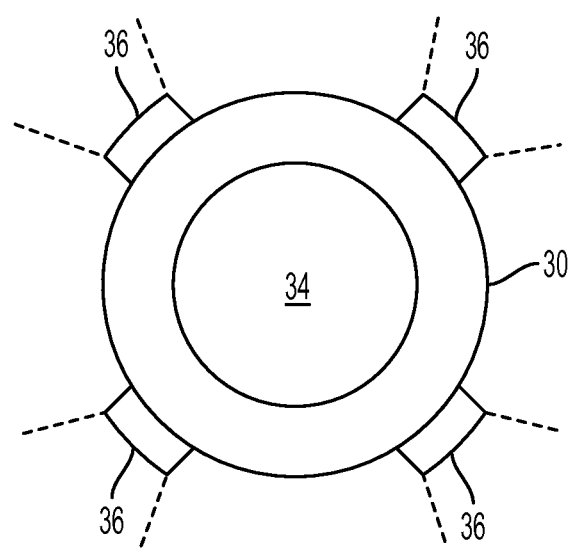
FIG. 3B is a schematic drawing of a cross-section view of the imaging catheter of FIG. 3A.

With reference to FIGS. 3A and 3B, in another embodiment, the imaging catheter 30 includes an array of multiple ultrasonic transducers 36 arranged around the perimeter of the distal end 34 of the catheter 30. For example, the transducers 36 can be positioned around at least a portion of the circumference or perimeter of the distal end 34 of the imaging catheter 30. In some embodiments, the multiple transducers 36 are configured to emit multiple signals or pulses in the radial direction to produce a 360 degree image of structures surrounding the catheter 30. Obtaining images in the radial direction is especially beneficial when the catheter 30 passes through a tubular structure such as a vein or artery. Specifically, radial facing transducers 36 can obtain images of the sidewalls of tubular structures, such as a vein or artery, without needing to reposition the catheter 30 as each image is obtained. In contrast, to obtain an image of a sidewall with a forward facing catheter 30, a user must orient the catheter 30 beam toward the sidewall and rotate the catheter 30 to obtain the 360 degree image. An exemplary intravascular ultrasound catheter with radially emitting ultrasound transducers is manufactured by Volcano Corporation of San Diego, Calif.

Figure 4:
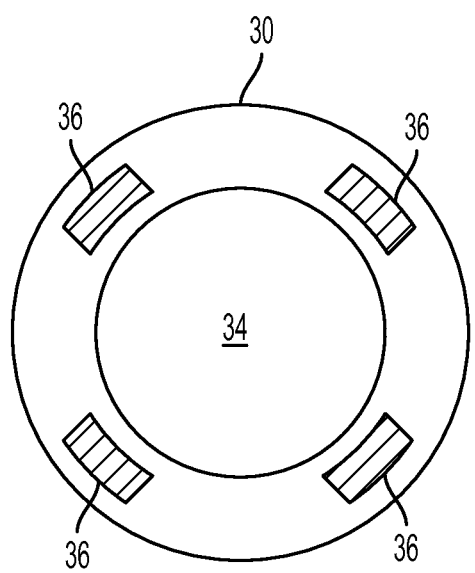
FIG. 4 is a schematic drawing of an embodiment of an imaging catheter.

With reference to FIG. 4, in another embodiment, a plurality of transducers 36 are positioned on the distal face of the catheter 30, such that ultrasound pulses emitted by the transducers 36 run parallel to the distal tip of the transseptal catheter 16 and transseptal introducer 18. Specifically, the plurality of transducers 36 are configured to emit ultrasonic pulse in the axial direction so that structures in front of the imaging catheter 30 can be imaged and identified. Alternatively, the transducers 36 can be positioned on a sidewall of the catheter 30 and either angled or bent in the forward direction so that the ultrasonic pulse generated by the transducer is emitted in the axial direction.

With reference again to FIGS. 1 and 2, the system 10 can also include sensors for measuring physical parameters of the patient, including physical parameters in the right and/or left atrium. For example, a pressure sensor 46 can be positioned on the patient cannula 12 or transseptal catheter 16 for measuring atrial pressure. Pressure measurements obtained by the pressure sensor 46 can be used to confirm when the transseptal catheter 16 enters the left atrium. Various other physiological sensors, including temperature sensors, oxygen sensors, or sensors for measuring flow rate can also be positioned along the catheters 12, 16 for obtaining additional physiological data.

Figure 5:
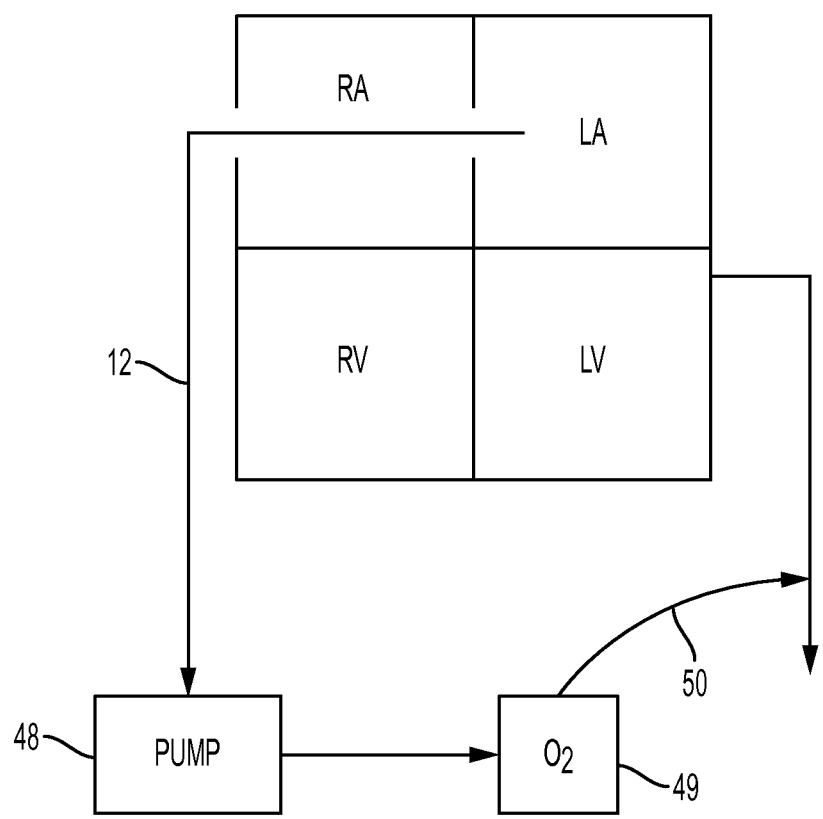
FIG. 5 is a schematic drawing of a system for left ventricular bypass including a patient cannula inserted to a left atrium of a patient.

With reference to FIG. 5, the system 10 can further include apparatus for providing therapeutic treatment for a patient. For example, once the patient cannula 12 is inserted to the left atrium through the atrial septum, the proximal end or hub 14 of the patient cannula 12 can be connected to an inflow port of a fluid pump 48. The pump 48 can be any centrifugal, axial, mixed, or roller pump, as is known in the art, that produces adequate flow rates through the system to achieve desired therapeutic results (e.g., either cardiac assist or left ventricular bypass). In certain embodiments of the system 10, the pump 48 can be secured to the patient via a holster secured around a patient's leg. The system 10 can also include an arterial cannula 50 disposed in a patient's artery. The arterial cannula 50 can be connected to an outflow portion of the pump 48, such that oxygenated blood flows from the left atrium LA through the patient cannula 12 to the external pump 48. The oxygenated blood is then introduced to the artery through the arterial cannula 50. In this way, the left ventricle LV is effectively bypassed providing assistance or rest for the left ventricle LV. In certain embodiments, the system 10 can be configured to provide extracorporeal membrane oxygenation (ECMO). More specifically, the system 10 can further include an oxygenator 49 connected in series with the pump 48. The oxygenator 49 receives blood from the pump 48, oxygenates the blood, and provides the oxygenated blood to an artery via the arterial cannula 50. The oxygenator 49 can be a spiral wound sheet membrane type or hollow fiber membrane type oxygenator, such as, the Terumo Capiox, Medtronic Minimax, Medtronic ECMO Oxygenators, Medtronic Affinity, Jostra Quadrox, Gish Vision, Cobe Optima, and others.

Figure 7A:
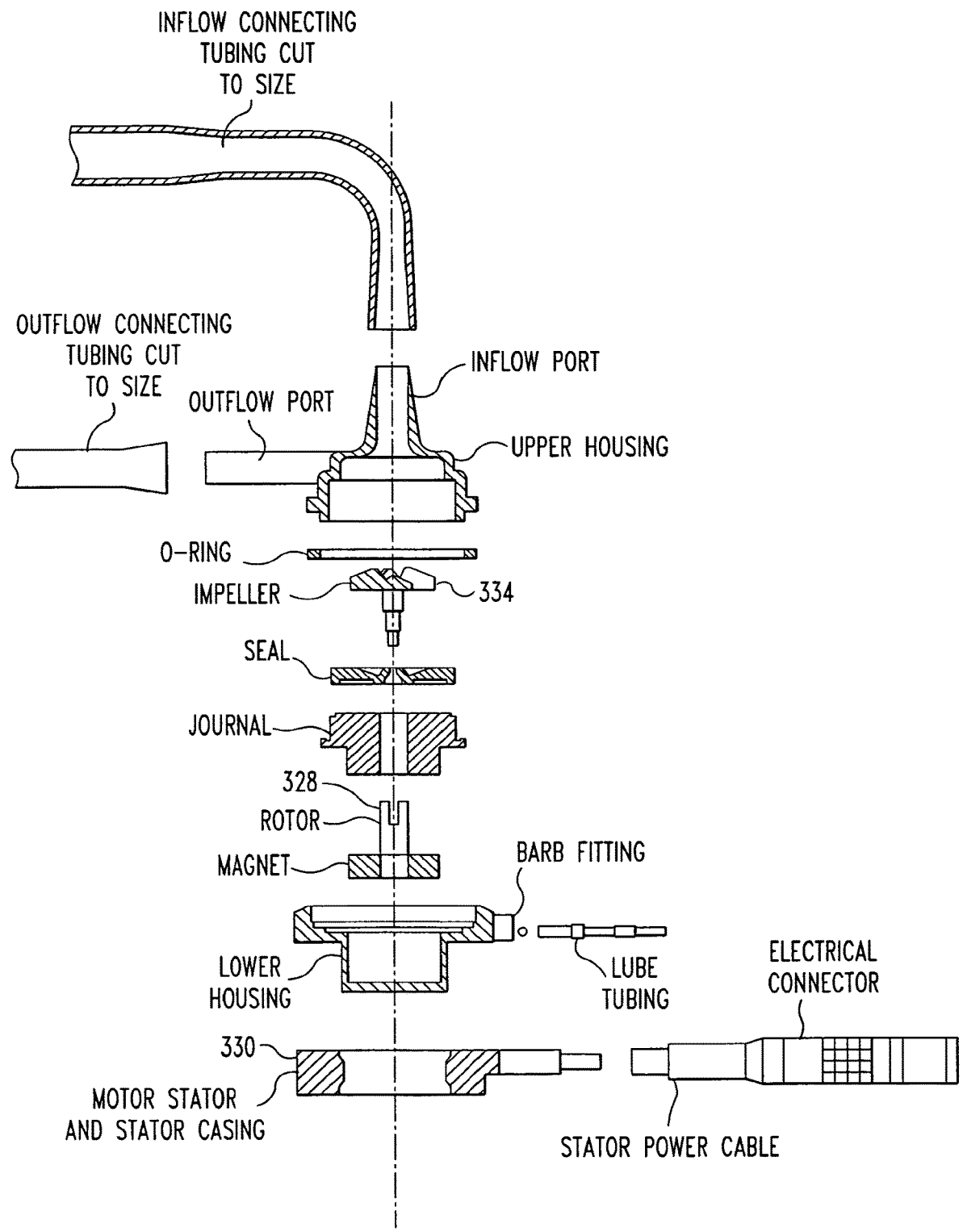
FIG. 7A is a schematic expanded view of a blood pump for use in the system of FIG. 5.
Figure 7B:
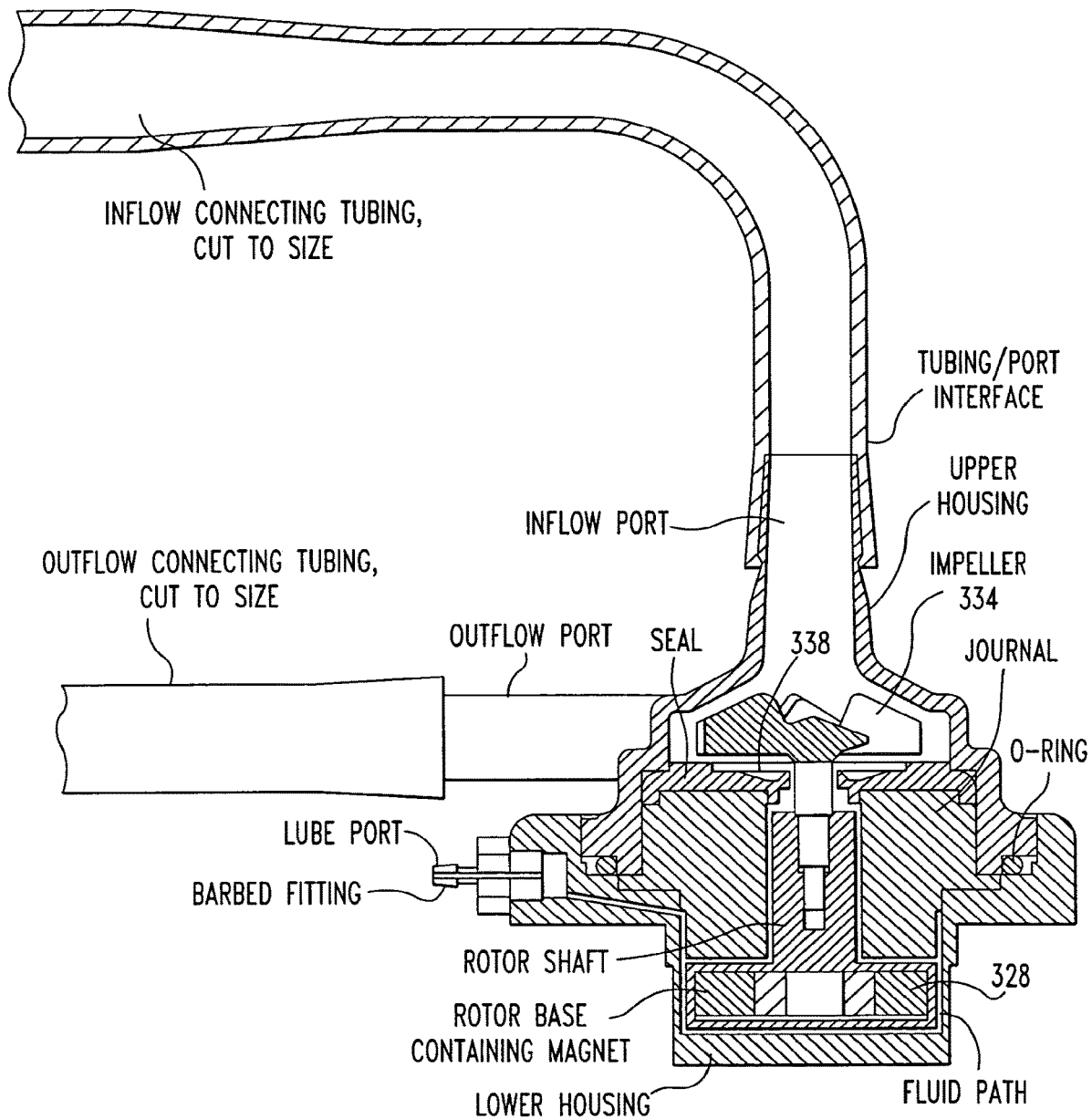
FIG. 7B is a schematic cross section view of the blood pump of FIG. 7A.

With reference to FIGS. 7A and 7B, a blood pump 316 that can be used with the above-described treatment system is illustrated. Preferably, the blood pump 316 pumps a continuous flow of blood. The blood pump 316 includes a rotor 328 and a stator 330. The blood pump 316 also includes an impeller 334 which moves against the blood. An operator or user adjusts the operation of the blood pump 316 by changing impeller 334 speed. Preferably, a controller measures flow of blood from the pump 316 based on the impeller 334 speed and stator 330 current. Alternatively, electromagnetic or ultrasonic flow probes in communication with the blood pump 316 can be used to measure flow of blood through the pump 316.

Preferably, the pump has a hydrodynamic bearing 338 between the rotor 328 and the lower housing, as shown in FIG. 7B. The blood pump 316 can be connected to a fluid reservoir and a fluid pump (not shown) to pump fluid from the reservoir to the blood pump 316 through the hydrodynamic bearing 338. Preferably, the fluid reservoir includes predetermined concentrations of a therapeutic agent or drug. The blood pump 316 can then be used to pump blood in combination with the therapeutic agent or drug to the patient. See U.S. Pat. No. 6,808,508 to Zafirelis et al. and U.S. Pat. No. 5,711,753 to Pacella et al. for a more complete discussion of the blood pump 316, each of which is incorporated by reference herein in its entirety.

Figure 6A:
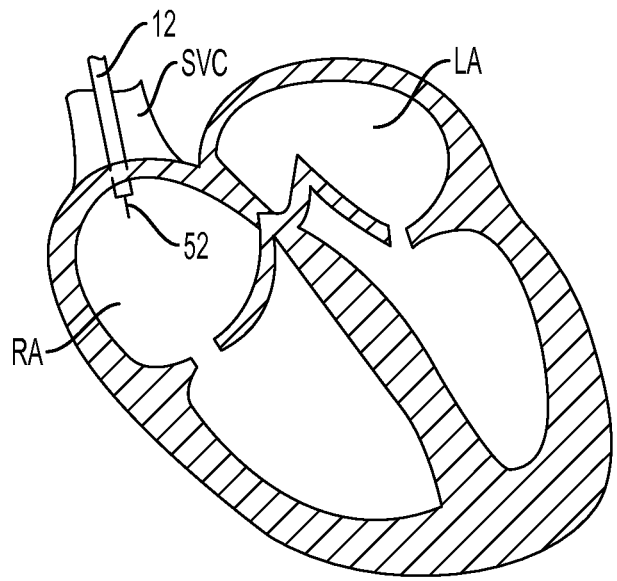
FIG. 6A is a schematic drawing of a human heart during a transseptal puncture procedure.
Figure 6B:
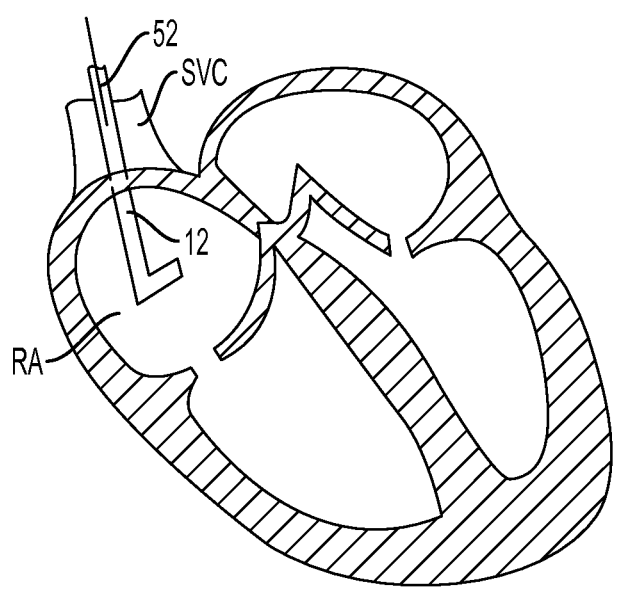
FIG. 6B is another schematic drawing of a human heart during a transseptal puncture procedure.
Figure 6C:
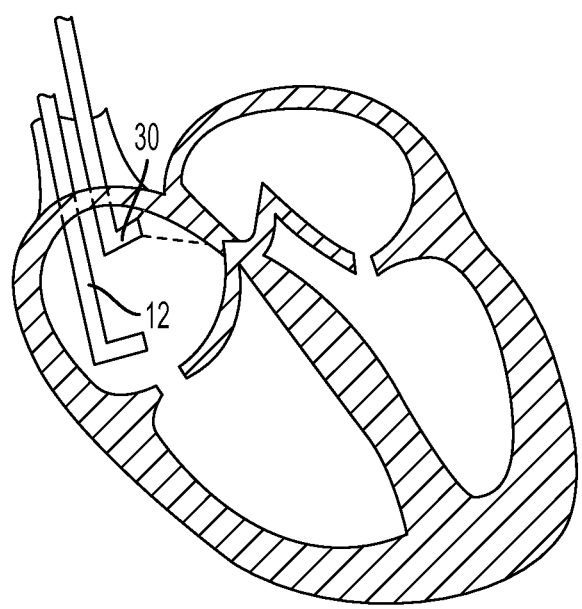
FIG. 6C is another schematic drawing of a human heart during a transseptal puncture procedure.

Having generally described the imaging system and cardiac assistance system, with reference to FIGS. 6A-6C, steps for obtaining an image of the atrial septum using an imaging catheter 30 and for performing a transseptal puncture based on the obtained images will now be discussed. While it is believed that a catheter 30 having axially emitting sensors or transducers 36 will provide a better quality images and require less manipulation of the catheter 30 position to obtain images of the atrial septum structure, the steps described herein may be used with any imaging catheter 30 including a single transducer catheter, a radial emitting transducer catheter, or an axially emitting transducer catheter.

As has been described previously, the catheters 16, 30 and patient cannula 12 are provided to the heart through the right femoral vein via percutaneous entry needle puncture. The vascular access site is often located near the groin, in alignment with the medial border of the femoral head. Initially, a guide wire 52 is inserted through the entry needle and is advanced to the superior vena cava SVC. The advancement of the guide wire 52 can be performed with the aid of fluoroscopic imaging techniques, as are known in the art. The guide wire 52 positioned in the superior vena cava SVC is illustrated in FIG. 6A. Once the guide wire 52 is in place in the superior vena cava SVC, a dilator can be used to serially dilate the percutaneous entry point. For example, a TandemHeart staged dilator with a gauge of from about 14 to 21 Fr can be used for this purpose. Once the percutaneous entry point is dilated a sufficient amount, the patient cannula 12, such as the TandemHeart transseptal cannula, is advanced over the guide wire 52 to the superior vena cava SVC. At this point in the process, the patient cannula 12 can have an obturator in place to seal the cannula 12 from receiving fluid.

While maintaining the guide wire 52 in the superior vena cava SVC, the distal end of the patient cannula 12 is advanced to the right atrium RA. More specifically, as shown in FIG. 6B, the user positions the cannula 12 at a 4:30 (e.g., about 45 degrees) position, so that the distal end of the cannula 12 points posterior and behind the aorta (not shown). Once the cannula 12 is in the requisite position, the cannula 12 is slowly pulled back until a drop from the superior vena cava SVC to the right atrium RA is noted by the user. Continuing to pull the cannula 12 moves the cannula 12 to a position along the lower third of the atrial septum just below the fossa ovalis of the atrial septum.

Once the cannula 12 is in the position adjacent to the atrial septum, an imaging catheter 30, such as the ultrasound catheter described herein, can be inserted through a hemostatic valve, located on the patient cannula 12, and over the guide wire 52 to advance the imaging catheter 30 to the superior vena cava SVC. At this point, the imaging catheter 30 can be slowly pulled back to advance from the superior vena cava SVC to the right atrium RA, in a similar manner as was described with the distal end of the patient cannula 12. The imaging catheter 30 and patient cannula 12 in the right atrium RA are illustrated in FIG. 6C. As the imaging catheter 30 is being pulled along the atrial septum, structures of the atrial septum, right atrium RA, and left atrium LA are imaged and identified by the user. The image data collected by the ultrasonic transducers can be provided to the signal processor and viewed by the user on the video display. When the thin portion of the fossa ovalis FO is identified on a display monitor, the user leaves the imaging catheter 30 in place, so that the imaging catheter 30 can continue to display and record images of the transseptal puncture procedure. However, if the preferred region of the fossa ovalis FO is not identified during a first pass, the process of pulling the imaging catheter 30 along the atrial septum can be repeated as necessary to obtain further ultrasonic images of the fossa ovalis FO and other structures.

Once the thin portion of the fossa ovalis FO is identified, a transseptal puncture procedure can be performed. During the transseptal puncture, the patient cannula 12 can be fixed in place within the right atrium. To perform the transseptal puncture, a second guide wire can be inserted through the hemostatic valve of the transseptal cannula and advanced through the right femoral vein to the superior vena cava SVC. At this point, a transseptal dilator, such as a Mullins dilator, can be inserted over the second guide wire and advanced to the superior vena cava SVC. Once the dilator is in position, the second guide wire can be removed. At this point, a needle, such as a Brockenbrough needle is inserted through the Mullins dilator for performing a standard transseptal puncture. As described above with respect to the patient catheter 12 and imaging catheter 30, the Mullins dilator and BRK apparatus tip are positioned at the 4:30 (e.g., 45 degree) position and slowly pulled or dragged from the superior vena cava SVC to the right atrium RA and from the high right atrium RA to the fossa ovalis FO. Since the imaging catheter 30 is still in place at a position at or slightly below the fossa ovalis FO, all movement of the Mullins dilator and BRK can be confirmed using the real time ultrasound images provided by the imaging catheter 30.

Figure 6D:
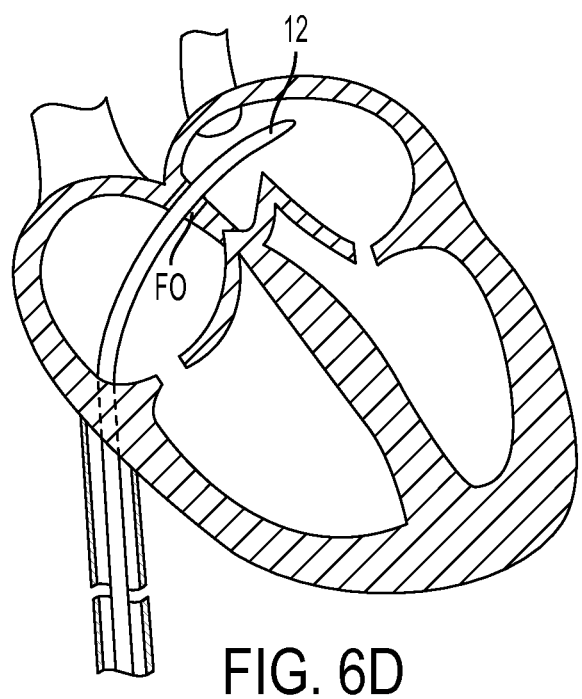
FIG. 6D is a schematic drawing of a human heart following a transseptal puncture procedure.

When the proper position of the transseptal puncture apparatus, namely the BRK needle and Mullins dilator, is confirmed through the ultrasound images, the BRK needle can be advanced through the fossa ovalis FO region of the atrial septum to perform the transseptal puncture. Following the puncture, the dilator can be advanced into the left atrium and the BRK needle can be removed, as is performed in a standard transseptal puncture technique. Next, an appropriate guide wire is inserted into the left atrium LA and the dilator can be removed from the left atrium. A dilator can be used to dilate the puncture through the atrial septum to a size sufficient to receive the patient cannula. An appropriate size can be about 21 Fr. At this point, the imaging catheter 30 and guide wire 52 can be removed. Finally, the transseptal cannula is advanced to the left atrium LA and positioned in a central portion of the left atrium LA. The cannula guide wire can then be removed leaving the cannula in place to provide fluid access to the left atrium LA. The patient cannula 12 positioned in the central portion of the left atrium LA is illustrated in FIG. 6D. Once the cannula 12 is in place, an arterial cannula can be inserted into a patient's artery. Then the patient cannula 12 and arterial cannula can be connected to an external pump, as described above. The pump can be actuated to begin a cardiac assist or bypass procedure.

It is understood that the above described method for accessing the left atrium LA can also be used for performing surgical, therapeutic, and diagnostic procedures in the left atrium. For example, once access to the left atrium LA is obtained, various surgical instruments can be provided to the left atrium LA through a catheter extending through the atrial septum. These items can be used to perform procedures including treatment or removal of the left atrial appendage, electrophysilogy (EP) ablation, heart catheterization, hemodynamic monitoring, mitral valve repair or replacement, or treatment of para-valvular leaks, using currently known techniques and processes.

While specific embodiments have been described in detail in the foregoing, it will be appreciated by those skilled in the art that various modifications and alternatives to those details could be developed in light of the overall teachings of the disclosure. Accordingly, the particular arrangements disclosed are meant to be illustrative only and not limiting as to the scope of invention. Further, although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A catheter assembly for performing a puncture of an anatomical wall, the catheter assembly comprising:
   a patient cannula configured to be drawn along a catheter and/or guide wire;
   a puncture catheter configured to be at least partially enclosed within the patient cannula and adapted to extend from the patient cannula to puncture the anatomical wall, wherein the puncture catheter includes a transseptal needle, and wherein the puncture catheter is configured such that forcing both the transseptal needle and the puncture catheter through the anatomical wall creates an opening through the anatomical wall;
   an imaging catheter comprising a plurality of transducers located around an outer surface of a distal portion of the imaging catheter, wherein at least one transducer of the plurality of transducers is configured to emit an energy beam in an axial direction, the energy beam being configured to reflect from a portion of the anatomical wall, and being further configured to detect energy reflected from the anatomical wall providing a measurement of a thickness of a section of the anatomical wall, wherein the energy beam emitted from the at least one transducer of the plurality of transducers comprises at least one of ultrasonic waves, radio waves, visible light waves, infrared waves, ultraviolet waves, any combination thereof, or an electro-magnetic signal, wherein the plurality of transducers are configured to obtain a 360 degree image, the plurality of transducers being configured to emit an energy beam in a radial direction relative to a longitudinal axis of the imaging catheter; and a transmitter configured to convey a signal representative of the energy detected by the at least one transducer of the plurality of transducers to a signal processor, wherein the signal includes the measurement of the thickness of the section of the anatomical wall, the transmitter further configured to obtain information from the signal which visually distinguishes thickness of different portions of the anatomical wall, to identify a thinnest portion of the anatomical wall, wherein the puncture catheter is configured to be positioned to puncture the thinnest portion of the anatomical wall, wherein the information includes a real time image of the anatomical wall, and to confirm, using the real time image, a positioning of the puncture catheter and transseptal needle with respect to the thinnest portion of the anatomical wall and movement of the puncture catheter and transseptal needle into the thinnest portion of the anatomical wall to create the opening in the anatomical wall;

wherein the patient cannula is configured to be advanced directly over the puncture catheter and to extend through the opening through the anatomical wall formed by the puncture catheter while the puncture catheter is configured to remain within the opening through the anatomical wall.

2. The catheter assembly of claim 1, wherein the imaging catheter is enclosed within, co-formed, or integrated with the patient cannula.

3. The catheter assembly of claim 1, wherein the imaging catheter extends parallel with and is connected to an outer surface of the patient cannula.

4. The catheter assembly of claim 1, wherein the at least one transducer of the plurality of transducers is located on a distal face of the imaging catheter.

5. An imaging system comprising:
a catheter assembly for performing a puncture of an anatomical wall, the catheter assembly comprising:
    a patient cannula configured to be drawn along a catheter and/or guide wire;
    a puncture catheter configured to be at least partially enclosed within the patient cannula and adapted to extend from the patient cannula to puncture the anatomical wall, wherein the puncture catheter includes a transseptal needle, and wherein the puncture catheter is configured such that forcing both the transseptal needle and the puncture catheter through the anatomical wall creates an opening through the anatomical wall;
    an imaging catheter comprising a plurality of transducers located around an outer surface of a distal portion of the imaging catheter, wherein at least one transducer of the plurality of transducers is configured to emit an energy beam in an axial direction, the energy beam being configured to reflect from a portion of the anatomical wall, and being further configured to detect energy reflected from the anatomical wall providing a measurement of a thickness of a section of the anatomical wall, wherein the energy beam emitted from the at least one transducer of the plurality of transducers comprises at least one of ultrasonic waves, radio waves, visible light waves, infrared waves, ultraviolet waves, any combination thereof, or an electro-magnetic signal, wherein the plurality of transducers are configured to obtain a 360 degree image, the plurality of transducers being configured to emit an energy beam in a radial direction relative to a longitudinal axis of the imaging catheter; and
    a transmitter configured to convey a signal representative of the energy detected by the at least one transducer of the plurality of transducers, the signal including the measurement of the thickness of the section of the anatomical wall; and
a signal processor configured to receive the signal from the transmitter, to obtain information from the signal which includes the thickness of the anatomical wall, for visually distinguishing thickness of different portions of the anatomical wall, to identify a thinnest portion of the anatomical wall, wherein the puncture catheter is configured to be positioned to puncture the thinnest portion of the anatomical wall, wherein the information includes a real time image of the anatomical wall, and to confirm, using the real time image, a positioning of the puncture catheter and transseptal needle with respect to the thinnest portion of the anatomical wall and movement of the puncture catheter and transseptal needle into the thinnest portion of the anatomical wall to create the opening in the anatomical wall;
wherein the patient cannula is configured to be advanced directly over the puncture catheter and to extend through the opening through the anatomical wall while the puncture catheter is configured to remain within the opening through the anatomical wall.

6. The imaging system of claim 5, further comprising a power supply, wherein power provided by the power supply is conveyed to the at least one transducer of the plurality of transducers through the transmitter.

7. The imaging system of claim 5, further comprising a visual and/or audio display configured to receive information about the thickness of portions of the anatomical wall and real time image of the anatomical wall from the signal processor to provide the information to an operator.

8. The imaging system of claim 5, wherein the imaging catheter is enclosed within, co-formed, or integrated with the patient cannula.

9. The imaging system of claim 5, wherein the imaging catheter extends parallel with and is connected to an outer surface of the patient cannula.

10. The imaging system of claim 5, wherein the at least one transducer of the plurality of transducers is located on a distal face of the imaging catheter.

11. The catheter assembly of claim 1, wherein the puncture catheter defines a first lumen and the imaging catheter defines a second lumen configured to be separate from and parallel to the first lumen, such that the imaging catheter is configured to be positioned to capture images of the distal portion of the puncture catheter.

12. The imaging system of claim 5, wherein the puncture catheter defines a first lumen and the imaging catheter defines a second lumen configured to be separate from and parallel to the first lumen, such that the imaging catheter is configured to be positioned to capture images of the distal portion of the puncture catheter.

* * * * *